(12) United States Patent
Singh et al.

(10) Patent No.: US 11,975,000 B1
(45) Date of Patent: May 7, 2024

(54) TADALAFIL ORAL TRANSMUCOSAL FILM

(71) Applicant: Xiamen LP Pharmaceutical Co., Ltd., Xiamen (CN)

(72) Inventors: Avinash Singh, Xiamen (CN); Rongbin Ling, Xiamen (CN); Liyuan Chen, Xiamen (CN); Fuxiang Lin, Xiamen (CN); Haijian Zhu, Xiamen (CN)

(73) Assignee: XIAMEN LP PHARMACEUTICAL CO., LTD., Xiamen (CN)

( * ) Notice: Subject to any disclaimer, the term of this patent is extended or adjusted under 35 U.S.C. 154(b) by 0 days.

(21) Appl. No.: 18/506,961

(22) Filed: Nov. 10, 2023

(30) Foreign Application Priority Data

Oct. 23, 2023 (CN) .......................... 202311378329.7

(51) Int. Cl.
| | | |
|---|---|---|
| *A61K 31/4985* | (2006.01) | |
| *A61K 9/00* | (2006.01) | |
| *A61K 47/06* | (2006.01) | |
| *A61K 47/10* | (2017.01) | |
| *A61K 47/12* | (2006.01) | |
| *A61K 47/26* | (2006.01) | |
| *A61K 47/28* | (2006.01) | |
| *A61K 47/36* | (2006.01) | |
| *A61K 47/38* | (2006.01) | |
| *A61K 47/40* | (2006.01) | |

(52) U.S. Cl.
CPC .......... *A61K 31/4985* (2013.01); *A61K 9/006* (2013.01); *A61K 47/06* (2013.01); *A61K 47/10* (2013.01); *A61K 47/12* (2013.01); *A61K 47/26* (2013.01); *A61K 47/28* (2013.01); *A61K 47/36* (2013.01); *A61K 47/38* (2013.01); *A61K 47/40* (2013.01)

(58) Field of Classification Search
CPC .... A61K 31/4985; A61K 9/006; A61K 47/06; A61K 47/10; A61K 47/12; A61K 47/26; A61K 47/28; A61K 47/36; A61K 47/38; A61K 47/40
See application file for complete search history.

(56) References Cited

U.S. PATENT DOCUMENTS

| | | | |
|---|---|---|---|
| 11,116,769 B2 | 9/2021 | Jeon et al. | |
| 2007/0020330 A1* | 1/2007 | Dang ..................... | A61K 31/56 514/217.05 |
| 2012/0156229 A1* | 6/2012 | Park ....................... | A61K 31/09 424/184.1 |
| 2016/0243036 A1* | 8/2016 | Paiement ............. | A61K 31/704 |

* cited by examiner

*Primary Examiner* — Frederick F Krass
*Assistant Examiner* — Lucy M Tien
(74) *Attorney, Agent, or Firm* — Perkins Coie LLP; Viola T. Kung

(57) ABSTRACT

The present invention provides an oral transmucosal film for delivering tadalafil through the buccal mucosa or sublingual mucosa. The film is a single layer structure containing amorphous tadalafil, one or more solubilizers, one or more penetration enhancers, and one or more adhesives to deliver the drug through a transmucosal route. Comparing with an oral tadalafil tablet, the present oral transmucosal film provides improved absorption rate and Tmax. The oral transmucosal film comprises 5%-60% by weight of amorphous tadalafil, 25-96% by weight of a film-forming material, 1-20% by weight of a solubilizer, 0.5-10% by weight of a penetration enhancer, and 1-15% by weight of an adhesive.

17 Claims, No Drawings

TADALAFIL ORAL TRANSMUCOSAL FILM

This application claims the priority of Chinese Application No. 202311378329.7, filed Oct. 23, 2023; which is incorporated herein by reference in its entirety.

FIELD OF INVENTION

The present invention relates to an oral transmucosal film for delivering tadalafil through the through the buccal mucosa or sublingual mucosa.

BACKGROUND OF THE INVENTION

Erectile dysfunction is the inability to get and keep an erection firm enough for sex. If it is an ongoing issue, can cause stress, affect self-confidence and contribute to relationship problems. Problems getting or keeping an erection can also be a sign of an underlying health condition that needs treatment and a risk factor for heart disease. It is a common condition in men aged over 40 years old, with the prevalence increasing with age. It has a variety of causes and is often treatable. If untreated, it can be the source of severe emotional stress to both patient and partner. Erectile dysfunction may be a symptom of a wide range of underlying pathologies that affects penile arteries, nerves, hormone levels, smooth muscle tissue, corporal endothelium, or tunica albuginea. Erectile dysfunction may be closely related to cardiovascular disease, diabetes mellitus, hyperlipidemia, hypertension, and other disorders.

World Health Organization (WHO) recommends oral drug treatment as the first-line treatment method, and phosphodiesterase 5 (PDE5) inhibitor is the first choice of an oral drug. Oral PDE5 inhibitors are the most widely used treatments for erectile dysfunction. Drugs known as PDE type-5 inhibitors increase penile blood flow. Oral agents approved in the United States by the Food and Drug Administration for treating ED include Viagra® (sildenafil citrate), Levitra® (vardenafil HCl), Cialis® (tadalafil), Stendra® (avanafil).

The chemical name of tadalafil is (6R-trans)-6-(1,3-benzodioxol-5-yl) 2,3,6,7,12,12a-hexahydro-2-methyl-pyrazino [1',2':1,6]pyrido[3,4-b]indole-1,4-dione. Tadalafil (CAS #171596-29-5) has a structure represented as below:

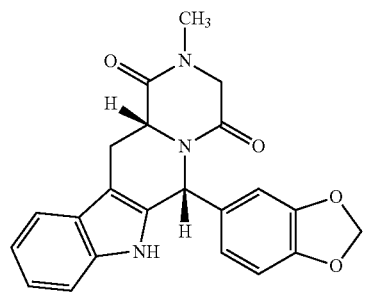 [SMILES: CN1CC(=O)N2[C@H](c3ccc4c(c3)OCO4)c3[nH]c4ccccc4c3C[C@@H]2C1=O]

Tadalafil is a crystalline solid that is practically insoluble in water and slightly soluble in some organic solvents such as methanol, ethanol and acetone. U.S. Pat. No. 6,841,167 discloses tadalafil having a water solubility of about 2 µg/mL in water at 25° C.

Tadalafil is one of the most widely used drug in oral agents for treating erectile dysfunction. Tadalafil has the longest duration of action (24-36 hours) in the class and a reported maximum duration of 72 hours. Tadalafil was developed by Eli Lilly for the treatment of male Erectile dysfunction (ED). It is a selective reversible inhibitor of the second generation phosphodiesterase 5 (PDE5). In 2003, it was approved by the FDA in the United States under the trade name CIALIS. Compared with similar marketed drugs sildenafil and vardenafil, tadalafil has the advantages of high selectivity and long half-life; tadalafil is now the first choice for Erectile dysfunction. Tadalafil is approved for once daily use for the treatment of ED and benign prostate hyperplasia.

CIALIS is available in 4 strengths from 2.5 to 20 mg. CIALIS is an immediate release tablet, the product is clinically efficacious, but the tablet dosage form has disadvantage of Tmax mean being 2 hours but varied from 30 min to 7 hours. The Cmax (maximum drug concentration in blood) of 20 mg tadalafil administered orally attains at a median of time 2 hours.

Tadalafil is a highly insoluble drug and is absorbed after oral administration and the mean maximum observed plasma concentration (Cmax) is achieved at a median time of 2 hours after dosing. The time of dosing (morning versus evening) has no clinically relevant effects on the rate and extent of absorption. The mean bioavailability of the tadalafil 20 mg oral tablet is about 88% relative to an oral suspension dosage form. This indicates the bioavailability of tadalafil oral tablet is good. However, Tmax of the tadalafil tablet is high, and the onset of action is long, which is contrary to a consumer's need.

There exists a need for a pharmaceutical composition for delivering tadalafil with a short Tmax and quick onset of action. The pharmaceutical composition should achieve rapid dissolution, uniformity, stability, and patient compliance.

DETAILED DESCRIPTION OF THE INVENTION

The inventors have discovered a pharmaceutical composition suitable for oral administration of tadalafil with faster absorption and quick onset of action. The pharmaceutical composition is an oral transmucosal film. The tadalafil oral transmucosal film of the present invention adheres to the buccal or sublingual mucosa and disintegrates or dissolves by the saliva within a few minutes, and tadalafil is absorbed directly into the blood vessels via mucosa, which avoids gastrointestinal degradation and bypasses the liver first pass effect, and consequently the absorption rate is improved dramatically comparing with tadalafil oral tablets. Transmucosal films are convenient to carry and use, suitable for patients who are difficult to swallow, and improve patient compliance.

Buccal epithelium is a relatively permeable non-keratinized tissue, where blood vessels drain directly into the jugular vein. The oral transmucosal film of the present invention promotes the absorption of tadalafil immediately and reduces Tmax. The oral transmucosal film of the present invention is designed to achieve faster absorption and quick onset of action by reducing the Tmax. The oral transmucosal film of the present invention is suitable for transmucosal delivery of tadalafil with an improved Tmax.

The invention provides a tadalafil transmucosal film has drug uniformity, good dissolution rate, good absorption rate, and acceptable taste. The dissolution of tadalafil is improved by selecting excipients and using organic solvents during manufacturing. The tadalafil transmucosal film of the present invention has good stability and palatability. The tadalafil transmucosal film is absorbed through the buccal or sublingual mucosa into blood, which reduces the time to reach a peak plasma concentration (Tmax), comparing to that of tadalafil oral tablets. Tadalafil in the present invention enters bloodstream through absorption so the administration is not affected by food.

The oral tadalafil transmucosal film of the present invention comprises about 5%-60% by weight of amorphous tadalafil, or a pharmaceutically acceptable salt thereof, about 25-96% by weight of a film-forming material, about 1-20% by weight of a solubilizer, about 0.5-10% by weight of a penetration enhancer, about 1-15% by weight of an adhesive, and optionally a sweetening agent and a plasticizer.

"A pharmaceutically acceptable salt," as used herein, is a salt that retain the desired biological activity of the parent compound and do not impart undesired toxicological effects.

"About" when used in this application, refers to ±10% of the recited value.

Unless otherwise specified, % used in this application refers to weight by weight %.

The active ingredient in the pharmaceutical composition is tadalafil free base or a pharmaceutically acceptable salt thereof, e.g., tadalafil salicylate, tadalafil mandelate. A preferred form of tadalafil is tadalafil free base. The amount of tadalafil in the film is about 1-50 mg, preferably 2-40 mg, 2.5-30 mg, or 2.5-20 mg.

Tadalafil is in an amorphous state in the film. The inventor discovered that when amorphous tadalafil is used in preparing a transmucosal film, the drug is rapidly dissolved and absorbed at faster absorption rate, comparing with a crystalline form of tadalafil in a transmucosal film.

The film-forming materials in the film include but are not limited to one or more of hypromellose (HPMC), hydroxypropyl cellulose (HPC), polyethylene glycol and polyvinyl alcohol graft copolymer (PEG-PVA), polyvinyl alcohol (PVA), polyvinyl pyrrolidone (PVP), hydroxyethyl cellulose, pullulan, sodium carboxymethyl cellulose (CMC-Na), xanthan gum, tragacanth gum, guar gum, polyacrylic acid, methylmethacrylate copolymer, high amylose starch, hydroxypropylated high amylose starch, collagen, gelatin, pectin, copovidone, povidone, and guar gum. Preferred film forming materials are HPMC, HPC, PEG-PVA, PVA, PVP, hydroxyethyl cellulose, and pullulan. The amount of the film-forming materials is about 25-96% w/w, 30-96% w/w, 35-96% w/w, 30-95% w/w, 25-80% w/w, 30-80% w/w, or 35-80% w/w. The film forming material has good compatibility with tadalafil and good drug loading capacity.

The present oral tadalafil transmucosal film selectively includes suitable excipients (a solubilizer, a penetration enhancer, and an adhesive) that contribute to faster dissolution and quick absorption of the drug.

The present oral transmucosal film includes one or more cyclodextrin (CD) derivatives as solubilizer. CDs are natural oligosaccharides possessing a hydrophilic exterior and hydrophobic cavity. CDs are obtained in three different forms: α-CD, β-CD, and γ-CD. CDs are used in encapsulation application since they can host active molecules through their internal hydrophobic cavities. Naturally occurring CDs are not freely soluble in water and most are only slightly soluble. The present film uses water-soluble CD derivatives to improve the solubility of tadalafil. Water-soluble CD derivatives form non-covalent inclusion complexes with tadalafil in a solution, which increases the solubility of tadalafil. Cyclodextrin derivatives include, but are not limited to: hydroxypropyl cyclodextrins, hydroxyethyl cyclodextrins, carboxyethylmethyl cyclodextrins, cyclomaltohexaose, cyclomaltoheptaose, 6-O-α-D-glucosyl-β-cyclodextrin, succinyl-β-cyclodextrin, and any combination thereof. In one preferred embodiment, hydroxypropyl derivatives of CD such as hydroxypropyl-β-cyclodextrin (HP-β-CD) is used as a solubilizer to increase the solubility and bioavailability of tadalafil. The film in general comprises about 1-20% by weight of cyclodextrin derivatives, preferably 2-12%.

One or more penetration enhancers are included in the present tadalafil film to improve the absorption rate of tadalafil into blood. Bile salts or chelating agents are included in the present film as a penetration enhancer. Bile salts are combination of a bile acid (steroid acid) with an amino acid (glycine or taurine). Bile salts are often used in a pharmaceutical preparation to enhance the absorption of low permeable drugs by the action of membrane fluidization, reverse micellization, or extraction of membrane protein or lipid. Bile salts used in the present tadalafil film include sodium glycocholate, sodium glycodeoxycholate, sodium taurodeoxycholate, sodium taurocholate, sodium taurodihydrofusidate, sodium glycodihydrofusidate, and any combination thereof. Chelating agents useful for the present tadalafil film include disodium EDTA, sodium citrate, methoxy salicylate, sodium salicylate and any combination thereof. The penetration enhancer used in the film is about 0.5-10% by weight, preferably 1-5% by weight or 1-3% by weight.

Bioavailability is affected by the rate of tadalafil absorbed through the oral mucosa and the time of the film adhering to the oral mucosa. To improve the adhesion and maximize the absorption, adhesives are added in the film. Suitable adhesives improve adhesion and do not affect tadalafil dissolution or reduce tadalafil bioavailability. Adhesives suitable for the present invention include one or more materials such as sodium alginate, chitosan derivative such as 5-methyl pyrrolidone chitosan, depolymerized chitosan, trimethyl chitosan, polyglutamic acid, polycarbophil, carbomer, dextran sulfate, chondroitin sulfate, sodium carboxyl methyl cellulose. Preferred adhesives are sodium alginate and chitosan derivative such as 5-methyl pyrrolidone chitosan, depolymerized chitosan, and trimethyl chitosan. The amount of adhesive in the film is 1-15% by weight preferably 1-10% by weight.

In one embodiment, the film further contains one or more plasticizers to improve the folding endurance of film and manufacturing processability. A suitable plasticizer includes polyethylene glycol (PEG), glycerin, sorbitol, or triethyl citrate. The amount of plasticizer is 0.5-10% by weight, preferably 0.75-8% by weight.

In one embodiment, the film further contains one or more sweeteners to improve the taste. Sweeteners of sweetening agents suitable for the present film include, but are not limited to, sucrose, glucose, sodium saccharin, fructose, xylitol, stevia, aspartame, sucralose, neotame, acesulfame potassium. The proportion of the above-mentioned taste modifying agent in the formulation is about 0.75-8% w/w, preferably about 0.75-4% w/w.

In one embodiment, the present tadalafil film comprises about 5-60% by weight of tadalafil or a pharmaceutical acceptable salt thereof, in an amorphous state, about 35-80% by weight of a film-forming material, 0.5-10% by weight of penetration enhancer, 1-10% by weight of adhesive, 2-12% by weight of a solubilizer. Optionally, the film further comprises 0.75%-4% by weight of a sweetening agent and 0.75%-8% by weight of a plasticizer. Tadalafil is in an amorphous state in the film.

Optionally the film further contains one or more pigments to improve the aesthetic appearance, such as titanium dioxide or those contained in FD&C or D&C.

The tadalafil transmucosal film is rapidly absorbed through the oral mucosa and enters the bloodstream. This application demonstrates that in pharmacokinetic studies carried out in beagle dogs, the Tmax of oral tablet was 3.2 hours, whereas the Tmax of the present tadalafil transmucosal film was 40 min to 70 min. Thus the present tadalafil transmucosal film reduces Tmax and accelerates the onset action.

The present invention provides a method for preparing a tadalafil oral transmucosal film. The insolubility of tadalafil makes the process of preparing tadalafil buccal film difficult. If tadalafil is not fully dissolved and is suspended in a solution, the hydrophobicity of tadalafil will lead to its aggregation and sedimentation in the solution, resulting in layer separation in the film forming solution. This layer separation and non-uniformity often occur during the film preparation process, including preparing a film forming solution, static defoaming, transporting, coating, and drying, which result in non-uniformity of tadalafil and poor appearance in the final product.

The present method for preparing tadalafil oral transmucosal film resolves the issues mentioned above. The present method comprises the following steps: (a) dissolving tadalafil or a pharmaceutical acceptable salt in an organic solvent, (b) mixing the film-forming material and other excipients of the formulation in a mixture of an organic solvent and water to form a first clear solution; (c) mixing (a) and (b) to form a second clear solution, (d) coating the second clear solution on a substrate and drying the second clear solution to form a film on the substrate; and (e) removing the film from the substrate, to form the oral transmucosal film of tadalafil. Tadalafil is almost insoluble in water, and soluble in certain organic solvents. The present method resolves the challenge of recrystallization of drug by selecting mixture of organic solvents with water. The selected solvent system solubilizes tadalafil completely and keeping an amorphous form of tadalafil in a transmucosal film. The amorphous form of tadalafil provides a good solubility and thus improving the absorption rate of tadalafil into blood.

In step (a), the organic solvent is selected from the group consisting of: dichloromethane, dimethyl sulfoxide, dimethyl formamide, and any combination thereof. A preferable organic solvent is dichloromethane.

In step (b) a preferred organic solvent is ethanol or isopropanol. The ratio of the organic solvent to water is about 2:1 to 4:1, for example, about 3:1.

In step (c), the mixture of (a) and (b) are mixed to form a clear solution. The ratio of organic solvents and water in the solution of (c) is about 1:1 to 5:1. This aqueous organic solvent mixture allows all materials to dissolve completely and form a homogeneous solution. Using a mixture of an organic solvent and water during preparation of the film results in tadalafil in an amorphous form in the film.

In step (d), the drying temperature is about 30°–100° C., preferably about 40-90° C.

In the present process, tadalafil is in an amorphous form in the film, which produces a faster dissolution rate and improve the absorption rate of tadalafil.

The substrate that the film formed on includes, but are not limited to, polyethylene terephthalate, polypropylene resins, and polymethylpentene resins.

After step (d), the film is optionally cut into a suitable size and shape, and then further wrapped or packaged.

The tadalafil transmucosal film of the present invention has a length of about 1-4 cm, and a width about 1-4 cm; preferably a length of about 1-3 cm, and width about 1-3 cm.

The present invention also provides a method for administering tadalafil to a subject. The method comprises identifying a subject in need thereof, and attaching the transmucosal film of the present invention to the buccal mucosa or sublingual mucosa of the subject. The method is suitable to treat erectile dysfunction, benign prostatic hyperplasia.

The present film is useful in treating a subject that is a mammal. The present invention is particularly useful in treating humans.

The following examples further illustrate the present invention. These examples are intended merely to be illustrative of the present invention and are not to be construed as being limiting.

EXAMPLES

Example 1: Tadalafil Film (Crystalline Form)

In this example, Tadalafil films were prepared according to the formulation and process below.

Formula:
Tadalafil 20.00 mg (33.33% w/w)
Hypromellose 26.00 mg (43.33% w/w)
Hydroxypropyl cellulose 12.30 mg (20.50% w/w)
Sodium lauryl sulfate 0.80 mg (1.33% w/w)
Sucralose 0.30 mg (0.50% w/w)
PEG 400 0.60 mg (1.00% w/w)
Purified water 60.00 mg
Manufacturing Process:
Dissolve Hypromellose, Hydroxypropyl cellulose, Sodium lauryl sulfate and Sucralose in water with continuous stirring, stir until clear solution forms.
Add tadalafil to the above solution and continue stirring for 25 minutes or until uniform suspension forms.
Add PEG 400 to the above suspension and stir for another 15 minutes.
Coat the defoamed film suspension in uniform thickness on a substrate,
Dry the coating at temperature of about 60° C. to 90° C. to form a film on the conveyor belt,
After the film was formed, cut the film into a suitable size, shape and packed in to pouch or in a suitable container.

Tadalafil film prepared according to the above formula and process had good film property, was easy to remove from the substrate, but the color was not uniform and patches were seen. In the dissolution test, the drug release was slow and incomplete due to the insolubility of crystalline drug.

TABLE 1

Dissolution Test Result of Example 1

| Media | 0.1N HCl, Volume 1000 ml, USP I basket method, rotation speed 100 rpm | | | | | | |
|---|---|---|---|---|---|---|---|
| Time (min) | 5 | 10 | 15 | 20 | 30 | 45 | 60 |
| Dissolved (%) | 5 | 8 | 11 | 20 | 23 | 27 | 28 |

Example 2: Tadalafil Film (Amorphous Film)

In this example, Tadalafil films were prepared in amorphous form, organic solvents used to solubilize the tadalafil.
Formula:
Tadalafil 20.00 mg (33.33% w/w)
Hypromellose 35.07 mg (58.45% w/w)
Hydroxypropyl β cyclodextrin (HP-β-CD) 4.00 mg (6.67% w/w)
Sucralose 0.30 mg (0.50% w/w)
PEG 400 0.60 mg (1.00% w/w)
FD&C Yellow No. 6 0.03 mg (0.050% w/w)
Dichloromethane (DCM) 12.00 mg
Ethanol 60.00 mg
Purified water 20.00 mg
Manufacturing Process:
Dissolve tadalafil in dichloromethane.
Dissolve all other excipients in water and ethanol mixture.
Mix both the drug solution and excipient solution and continue stirring until clear solution forms.
Coat the defoamed film solution in uniform thickness on a substrate,
Dry the coating at temperature of about 40° C. to 90° C. to form a film on the conveyor belt,
After the film was formed, cut the film into a suitable size, shape and packed in to pouch or in a suitable container.

Tadalafil film prepared according to the above formula and process had good film property, smooth appearance, was easy to remove from the substrate, and uniform in color, and blend uniformity was satisfactory. X-ray powder diffraction study shows that tadalafil was in amorphous state. In the dissolution test, the drug release was fast and complete.

TABLE 2

Dissolution Test Result of Example 2

| Media | 0.1N HCl, Volume 1000 ml, USP I basket method, rotation speed 100 rpm | | | | | | |
|---|---|---|---|---|---|---|---|
| Time (min) | 5 | 10 | 15 | 20 | 30 | 45 | 60 |
| Dissolved (%) | 50 | 80 | 88 | 93 | 96 | 96 | 97 |

The Tadalafil film prepared was compared with Tadalafil tablet in the pharmacokinetic study conducted in beagle dogs. The results showed that the film is bioequivalent to tablets. Tmax is shorter than tablet. See Example 8 for the experimental results.

The film did not attach to the mucosa throughout the administration process, and the film moved from the site of attachment. Therefore, an adhesive was added in the formulation to help the attachment of the film to the mucosa.

At the same time, different concentrations of ethanol solution (30-70%), acetone solution (30-70%) were used to study without dichloromethane, the XRD study of these prepared films shows the API was in a crystalline form and the dissolution was not complete.

Example 3: Tadalafil Film (with Adhesive)

In this example, adhesives added to the Example 2 and different adhesives evaluated. Manufacturing process was same as Example 2.

| Formula: | | |
|---|---|---|
| Example | 3-1 | 3-2 |
| Tadalafil | 20.00 mg (33.33% w/w) | 20.00 mg (33.33% w/w) |
| Hypromellose | 33.42 mg (55.70% w/w) | 33.42 mg (55.70% w/w) |
| Sodium alginate (SA) | 1.65 mg (2.75% w/w) | — |
| 5-Methyl pyrrolidone Chitosan (MPC) | — | 1.65 mg (2.75% w/w) |
| (HP-β-CD) | 4.00 mg (6.67% w/w) | 4.00 mg (6.67% w/w) |
| Sucralose | 0.30 mg (0.50% w/w) | 0.30 mg (0.50% w/w) |
| PEG 400 | 0.60 mg (1.00% w/w) | 0.60 mg (1.00% w/w) |
| FD&C Yellow No. 6 | 0.03 mg (0.050% w/w) | 0.03 mg (0.050% w/w) |
| Dichloromethane (DCM) | 12.00 mg | 12.00 mg |
| Ethanol | 60.00 mg | 60.00 mg |
| Purified water | 20.00 mg | 20.00 mg |

The Tadalafil film prepared had smooth appearance, pale yellowish color. The X-ray powder diffraction study of the film showed that tadalafil was in an amorphous state. The dissolution experiment showed that 90% of drug dissolved in 10 minutes.

TABLE 3

Dissolution Test Result of example 3

| Media | 0.1N HCl, Volume 1000 ml, USP I basket method, rotation speed 100 rpm | | | | | | |
|---|---|---|---|---|---|---|---|
| Time (min) | 5 | 10 | 15 | 20 | 30 | 45 | 60 |
| Dissolved (%) | 60 | 90 | 93 | 95 | 97 | 99 | 99 |

The Tadalafil transmucosal films of Example 3 were used in animal studies and the films were bioequivalent to a reference tablet. Tmax of Example 3-1 was 1.70 hour and Tmax of Example 3-2 was 1.25 hour, this indicates that chitosan and sodium alginate improved the adhesion as well as absorption of drug through the mucosa. See Example 8 for the experimental results.

Example 4: Tadalafil Film (Bile Salts as Penetration Enhancer)

In this experiment, bile salts were added as penetration enhancer to shorten the Tmax, the other formulation details were same as example 3. The manufacturing process was similar to Example 2. All % shown below are w/w.

| Formulation: | | | | |
|---|---|---|---|---|
| Example | 4-1 | 4-2 | 4-3 | 4-4 |
| Tadalafil | 20.00 mg (33.33%) | 20.00 mg (33.33%) | 20.00 mg (33.33%) | 20.00 mg (33.33%) |
| Hypromellose | 35.02 mg (58.37%) | 29.02 mg (48.37%) | 28.47 mg (47.45%) | — |

-continued

| Example | 4-1 | 4-2 | 4-3 | 4-4 |
| --- | --- | --- | --- | --- |
| Hydroxy ethyl cellulose | — | — | — | 16.12 (26.87%) |
| PVP K30 | — | — | — | 12.00 (20.00%) |
| MPC | 1.65 mg (2.75%) | 1.65 mg (2.75%) | 6.00 mg (10.00%) | 1.65 mg (2.75%) |
| HP-β-CD | 1.50 mg (2.50%) | 7.5 mg (12.50%) | 4.00 mg (6.67%) | 7.5 mg (12.50%) |
| Sodium glycocholate (SGC) | 0.90 mg (1.50%) | 0.90 mg (1.50%) | — | — |
| Sodium taurodihydrofusidate (STDF) | — | — | 0.60 mg (1.00%) | 1.80 mg (3.00%) |
| Sucralose | 0.30 mg (0.50%) | 0.30 mg (0.50%) | 0.30 mg (0.50%) | 0.30 mg (0.50%) |
| PEG 400 | 0.60 mg (1.00%) | 0.60 mg (1.00%) | 0.60 mg (1.00%) | 0.60 mg (1.00%) |
| FD&C Yellow No. 6 | 0.03 mg (0.050%) | 0.03 mg (0.050%) | 0.03 mg (0.050%) | 0.03 mg (0.050%) |
| Dichloromethane | 12.00 mg | 12.00 mg | 12.00 mg | 12.00 mg |
| Ethanol | 60.00 mg | 60.00 mg | 60.00 mg | 60.00 mg |
| Purified water | 20.00 mg | 20.00 mg | 20.00 mg | 20.00 mg |

The tadalafil film prepared according to the above formulas had smooth appearance. The dissolution experiments of all examples showed more than 90% release of tadalafil in 10 minutes.

The Tadalafil transmucosal films of all examples were used in animal study, and the Tmax's were compared with oral RLD tablet. See Example 8 for the experimental results. The Tmax's of all the examples were within a range of 40-60 minutes. This indicates the presence of penetration enhancer improves the absorption rate. Example 4-2 is having fastest absorption of Tmax 40 min, followed by example 4-4 and 4-3.

Further, different adhesives were evaluated to prepare tadalafil transmucosal films. When polycarbophil and carbomer were used, the drug release was slower, about less than 75% in 15 min.

Example 5: Tadalafil Transmucosal Film (Chelating Agents as Permeation Enhancer)

In these experiments, chelating agents of sodium citrate and disodium EDTA were used as a permeation enhancer, and the other formulation details were same as described in previous examples. The manufacturing process was similar to example 2.

| Example | 5-1 | 5-2 |
| --- | --- | --- |
| Tadalafil | 20.00 mg (33.33% w/w) | 20.00 mg (33.33% w/w) |
| Hydroxypropyl cellulose | 22.62 mg (37.70% w/w) | 24.12 mg (40.20% w/w) |
| PVA-PEG copolymer | 9.00 mg (15% w/w) | 9.00 mg (10% w/w) |
| MPC | 1.65 mg (2.75% w/w) | 0.75 mg (1.25% w/w) |
| HP-β-CD | 4.00 mg (6.67% w/w) | 4.00 mg (6.67% w/w) |
| Sodium Citrate | 1.80 mg (3.00% w/w) | — |
| Disodium EDTA | — | 1.2 mg (2.00% w/w) |
| Sucralose | 0.30 mg (0.50% w/w) | 0.30 mg (0.50% w/w) |
| PEG 400 | 0.60 mg (1.00% w/w) | 0.60 mg (1.00% w/w) |
| FD&C Yellow No. 6 | 0.03 mg (0.050% w/w) | 0.03 mg (0.050% w/w) |
| Dichloromethane | 12.00 mg | 12.00 mg |
| Ethanol | 60.00 mg | 60.00 mg |
| Purified water | 20.00 mg | 20.00 mg |

The Tadalafil films prepared according to the above formulas had a smooth appearance. The dissolution experiments of both 5-1 and 5-2 batches showed that more than 90% drug was released in 15 minutes. The tadalafil transmucosal films of both the examples were used in animal studies, and the Tmax's were compared with oral RLD tablet. See Example 8 for the experimental results. There is no significant difference between the Tmax of example 5-1 and Example 5-2.

In comparison between a bile salt and a chelating agent as a permeation enhancer, there was no significant difference.

Different concentrations of disodium EDTA such as 1.5%, 2%, 2.5%, and 3% by weight were tested. The dissolution result shows that when the concentration was 2.5% and above, the release was slow and less than 70% release seen in 15 minutes.

Different concentrations of sodium citrate such as 2%, 3%, 4%, and 5% by weight were tested. Initial dissolution tests show that all batches had more than 90% tadalafil release in 15 minutes. After accelerated stability study of 6 months, batches with 4%, and 5% by weight of sodium citrate showed a drop of tadalafil release in dissolution tests to less than 75% in 15 minutes.

Example 6: Tadalafil Transmucosal Film (Fatty Acids as Permeation Enhancer)

Fatty acids are often used as a permeation enhancer. In Examples 6-1 and 6-2, different fatty acids were used as a permeation enhancer and tested. The manufacturing process was similar as described in Example 2. The formulation details are given below.

| Examples | 6-1 | 6-2 |
| --- | --- | --- |
| Tadalafil | 20.00 mg (33.33% w/w) | 20.00 mg (33.33% w/w) |
| Hypromellose | 32.67 mg (54.45% w/w) | 32.67 mg (54.45% w/w) |
| MPC | 1.65 mg (2.75% w/w) | 1.65 mg (2.75% w/w) |
| HP-β-CD | 4.00 mg (6.67% w/w) | 4.00 mg (6.67% w/w) |
| Oleic acid (OA) | 0.75 (1.25% w/w) | — |
| Lauric acid (LA) | — | 0.75 (1.25% w/w) |
| Sucralose | 0.30 mg (0.50% w/w) | 0.30 mg (0.50% w/w) |
| PEG 400 | 0.60 mg (1.00% w/w) | 0.60 mg (1.00% w/w) |
| FD&C Yellow No. 6 | 0.03 mg (0.050% w/w) | 0.03 mg (0.050% w/w) |
| Dichloromethane | 12.00 mg | 12.00 mg |
| Ethanol | 60.00 mg | 60.00 mg |
| Purified water | 20.00 mg | 20.00 mg |

Note:
The solvents used in the manufacturing process were removed during the process of drying.

Dissolution rates of tadalafil transmucosal films of Examples 6-1 and 6-2 were slow (less than 75% was dissolved in 15 min), and a complete release was not observed. The results indicate that the combination of cyclodextrin as a solubilizer with fatty acids as a permeation enhancer was not suitable.

TABLE 4

Dissolution Test Result of Example 6

| Media | 0.1N HCl Volume 1000 ml, USP I basket method, rotation speed 100 rpm | | | | | |
|---|---|---|---|---|---|---|
| Time (min) | 5 | 10 | 15 | 20 | 30 | 45 |
| Dissolved (%) (Example 6-1) | 35 | 53 | 69 | 72 | 83 | 84 |
| Dissolved (%) (Example 6-2) | 40 | 61 | 73 | 81 | 85 | 86 |

In similar experiments, other fatty acids such as medium chain triglyceride, span 80, polyoxyethylene 35 castor oil and oleoyl polyoxyl-6 glycerides were tested. The results show that, dissolution of these tadalafil films were slow and release of tadalafil was incomplete.

Example 7: Tadalafil Film (Plasticizer and Sweetener Evaluation)

The samples obtained from the Example 3-2 were subjected to a taste evaluation by 10 volunteers. The volunteers reported that that taste was acceptable but with a slight bitterness.

In this experiment, sweetener and plasticizer were evaluated, and the other formulation details were same as example 2. The manufacturing process was similar to example 2. All % shown below are w/w.

| | Formulation: | | | |
|---|---|---|---|---|
| Example | 7-1 | 7-2 | 7-3 | 7-4 |
| Tadalafil | 20.00 mg (33.33%) | 20.00 mg (33.33%) | 20.00 mg (33.33%) | 20.00 mg (33.33%) |
| Hypromellose | 32.37 mg (53.95%) | 30.42 mg (50.70%) | 32.52 mg (54.20%) | 28.17 mg (46.95%) |
| MPC | 1.65 mg (2.75%) | 1.65 mg (2.75%) | 1.65 mg (2.75%) | 1.65 mg (2.75%) |
| HP-β-CD | 4.00 mg (6.67%) | 4.00 mg (6.67%) | 4.00 mg (6.67%) | 4.00 mg (6.67%) |
| SGC | 0.90 mg (1.50%) | 0.90 mg (1.50%) | 0.90 mg (1.50%) | 0.90 mg (1.50%) |
| Sucralose | 0.45 mg (0.75%) | 2.40 mg (4.00%) | 0.45 mg (0.75%) | 0.45 mg (0.75%) |
| PEG 400 | 0.60 mg (1.00%) | 0.60 mg (1.00%) | 0.45 mg (0.75%) | 4.80 mg (8.00%) |
| FD&C Yellow No. 6 | 0.03 mg (0.050%) | 0.03 mg (0.050%) | 0.03 mg (0.050%) | 0.03 mg (0.050%) |
| Dichloromethane | 12.00 mg | 12.00 mg | 12.00 mg | 12.00 mg |
| Ethanol | 60.00 mg | 60.00 mg | 60.00 mg | 60.00 mg |
| Purified water | 20.00 mg | 20.00 mg | 20.00 mg | 20.00 mg |

Tadalafil films prepared according to the above formulae had good film property and smooth appearance. They were easy to remove from the substrate, and uniform in color, and the blend uniformity was satisfactory. In a dissolution test, the drug release was fast and complete.

Example 7-1 and Example 7-2 were used for taste evaluation study in 10 volunteers. Volunteers did not feel bitter or tongue irritation throughout the administration process and thus patient compliance was good.

In addition, films with a plasticizer concentration of 10% and 12% by weight were prepared. Films with these concentrations were very soft and the films took a long time to dry.

Example 8: Bioavailability Study of Tadalafil Transmucosal Film

In this example, pharmacokinetic parameters were tested and compared between oral tablet and the present transmucosal films. Tadalafil oral tablet 20 mg RLD (CIALIS) and tadalafil transmucosal films 20 mg of Examples 2, 3, 4, 5 and 6 were tested on beagle dogs. In the tadalafil film group, films containing 20 mg of tadalafil were administered on to the buccal mucosa, and the films were attached to the mucosa. In the tablet group, tadalafil RLD tablets (20 mg) were administered orally with water. Blood samples were withdrawn before administration (0 min) and 15 min, 30 min, 45 min, 1 h, 1.25 h, 1.5 h, 1.75 h, 2.0 h, 2.25 h, 2.5 h, 3.0 h, 4.0 h, 5.0 h and 6.0 h after administration. The concentrations of tadalafil in blood were determined by LC-MS/MS method, and the relative bioavailability and Tmax of each tadalafil film and RLD tablet was calculated and compared.

The results are shown in the following Table 4. The relative bioavailability of the transmucosal film of Example 2 was 82% and Tmax was 2.30 h. The relative bioavailability of each Example 3-1 and 3-2 was within acceptable criteria, and each Tmax was 1.70 and 1.25 h, respectively. The relative bioavailability of each Example 4-1 to 4-4 was within acceptable criteria, and each Tmax was 1 h, 40 min, 50 min and 45 minutes, respectively. The relative bioavailability of each Example 5-1 and 5-2 was within acceptable criteria, and each Tmax was 55 min and 1.15 h, respectively.

The pharmacokinetic results show that the transmucosal films of Examples 4-1 to 4-4 and Example 5-1 to 5-2 had a significantly faster absorption rate than that of an oral tablet. The comparison between Example 4 (4-1 to 4-4) and Example 5 (5-1 to 5-2) reveal that a bile salt as a penetration enhancer in combination with HP-β-CD have faster absorption than chelating agent as absorption enhancer with HP-β-

CD. Comparison between Examples 3-1 and 3-2 reveals that presence of chitosan (Example 3-2) as a bio adhesive improves the absorption and Tmax.

After evaluation of Tmax, Examples 4 (4-1 to 4-5) and 5 (5-1 to 5-2) with the presence of cyclodextrin as solubilizer, a permeation enhancer, and chitosan as a bioadhesive provides faster absorption rate with Tmax of 40-70 minutes, which are much shorter than the 3.20 h of Tmax of oral tablets. The results indicate that tadalafil in an amorphous form in the prepared film had faster absorption compared to reference RLD tablet.

TABLE 5

Bioavailability and Tmax Test results

| | Group | Tablet | Example 2 | Example 3-1 | Example 3-2 | Example 4-1 | Example 4-2 | Example 4-3 |
|---|---|---|---|---|---|---|---|---|
| | Dose | 20 mg | 20 mg | 20 mg | 20 mg | 20 mg | 20 mg | 20 mg |
| | Formulation characteristics | | Amorphous | SA adhesive | MPC adhesive | Adding SGC | Increase HP-β-CD | Adding STDF |
| P' kinetic | Tmax (Mean) | 3.20 h | 2.30 h | 1.70 h | 1.25 h | 1 h | 40 min | 50 min |
| | Relative bio-availability (%)* | 100% | 82% | 93% | 95% | 110% | 113% | 105% |

TABLE 6

Bioavailability and Tmax Test results

| | Group | Tablet | Example 4-4 | Example 5-1 | Example 5-2 |
|---|---|---|---|---|---|
| | Dose | 20 mg | 20 mg | 20 mg | 20 mg |
| | Formulation characteristics | | Decrease MPC | Adding Sodium Citrate | Adding EDTA |
| P' kinetic parameters | Tmax (Mean) | 3.20 h | 45 min | 55 min | 1.15 h |
| | Relative bioavailability (%)* | 100% | 92% | 105% | 109% |

$$*\text{Relative Bioavailability} = \frac{AUC_{film}}{AUC_{tablet}} \times \frac{\text{Dose}_{tablet}}{\text{Dose}_{film}} = \frac{AUC_{film}}{AUC_{tablet}} \times \frac{20 \text{ mg}_{tablet}}{20 \text{ mg}_{film}}$$

The invention, and the manner and process of making and using it, are now described in such full, clear, concise and exact terms as to enable any person skilled in the art to which it pertains to make and use the same. It is to be understood that the foregoing describes preferred embodiments of the present invention, and that modifications can be made therein without departing from the scope of the present invention as set forth in the claims. To particularly point out and distinctly claim the subject matter regarded as invention, the following claims conclude this specification.

What is claimed is:

1. An oral transmucosal film, comprising, 5%-60% by weight of amorphous tadalafil, 25-80% by weight of a film-forming material, 1-20% by weight of a solubilizer, 0.5-10% by weight of a penetration enhancer, and 1-15% by weight of an adhesive;
    wherein the film-forming material comprises hypromellose (HPMC), hydroxypropyl cellulose (HPC), polyethylene glycol and polyvinyl alcohol graft copolymer (PEG-PVA), polyvinyl alcohol (PVA), polyvinyl pyrrolidone (PVP), hydroxyethyl cellulose, pullulan, sodium carboxymethyl cellulose (CMC-Na), xanthan gum, tragacanth gum, guar gum, polyacrylic acid, methylmethacrylate copolymer, high amylose starch, hydroxypropylated high amylose starch, collagen, gelatin pectin, copovidone, povidone, or guar gum, or any combination thereof,
    the solubilizer is selected from the group consisting of: hydroxypropyl-β-cyclodextrins, hydroxyethyl cyclodextrins, carboxyethylmethyl cyclodextrins, cyclomaltohexaose, cyclomaltohepatose, 6-O-α-D-glucosyl-β-cyclodextrin, succinyl-β-cyclodextrin, and any combination thereof,
    the penetration enhancer is selected from the group consisting of: sodium glycocholate, sodium taurodihydrofusidate, sodium taurocholate, sodium glycodihydrofusidate, and any combination thereof; and
    the adhesive is selected from the group consisting of 5-methyl pyrrolidone chitosan, depolymerized chitosan, trimethyl chitosan, and any combination thereof.

2. The film according to claim 1, comprising, 5-60% by weight of amorphous tadalafil, 35-80% by weight of the film-forming material, 2-12% by weight of the solubilizer, 1-5% by weight of the penetration enhancer, and 1-10% by weight of the adhesive.

3. The film according to claim 1, wherein the film-forming material comprises HPMC, HPC, PEG-PVA, PVA, PVP, hydroxyethyl cellulose, or pullulan, or any combination thereof.

4. The film according to claim 1, wherein the solubilizer is hydroxypropyl-β-cyclodextrins or hydroxyethyl cyclodextrins.

5. The film according to claim 1, wherein the penetration enhancer is sodium glycocholate or, sodium taurodihydrofusidate.

6. The film according to claim 1, wherein the adhesive is 5-methyl pyrrolidone chitosan.

7. The film according to claim 1, wherein the film-forming material comprises HPMC, HPC, PEG-PVA, PVA, PVP, hydroxyethyl cellulose, or pullulan, or any combination thereof; the solubilizer is hydroxypropyl-β-cyclodextrins or hydroxyethyl cyclodextrins; the penetration enhancer is sodium glycocholate or sodium taurodihydrofusidate; and the adhesive is 5-methyl pyrrolidone chitosan.

8. The film according to claim 2, wherein the film-forming material comprises HPMC, HPC, PEG-PVA, PVA, PVP, hydroxyethyl cellulose, or pullulan, or any combination thereof; the solubilizer is hydroxypropyl-β-cyclodextrins or hydroxyethyl cyclodextrins; the penetration enhancer is sodium glycocholate or sodium taurodihydrofusidate; and the adhesive is 5-methyl pyrrolidone chitosan.

9. The film according to claim 1, comprising 2.5-25 mg of amorphous tadalafil.

10. The film according to claim 1, further comprising a plasticizer selected from the group consisting of: PEG 400, triethyl citrate, glycerin, or a combination thereof.

11. The film according to claim 10, comprising 0.5-8% w/w of the plasticizer.

12. The film according to claim 1, further containing one or more sweeteners.

13. The film according to claim 12, comprising 0.75-8% w/w of one or more sweeteners selected from the group consisting of: sucrose, glucose, sodium saccharin, fructose, xylitol, stevia, aspartame, sucralose, neotame, acesulfame potassium, and any combination thereof.

14. A process for preparing the oral transmucosal film according to claim 1, comprising the steps of:
(a) dissolving the amorphous tadalafil in a first organic solvent,
(b) mixing the film-forming material, the solubilizer, the penetration enhancer, and the adhesive in a mixture of a second organic solvent and water to form a first clear solution;
(c) mixing (a) and (b) to form a second clear solution,
(d) coating the second clear solution on a substrate and drying the second clear solution to form a film on the substrate; and
(e) removing the film from the substrate, to form the oral transmucosal film.

15. The method of claim 14, wherein the first organic solvent in step (a) is selected from the group consisting of: dichloromethane, dimethyl sulfoxide, dimethyl formamide, and any combination thereof.

16. The method of claim 14, wherein the second organic solvent is selected from the group consisting of ethanol and isopropanol.

17. A method for treating erectile dysfunction in a subject, comprising the steps of:
identifying a subject in need thereof, and
attaching the film of claim 1 to the buccal mucosa or sublingual mucosa of the subject.

* * * * *